United States Patent
Paganelli et al.

(10) Patent No.: US 7,935,346 B2
(45) Date of Patent: May 3, 2011

(54) MEDICAMENT FOR THE TWO-STEP PERIOPERATIVE THERAPY OF SOLID TUMOURS

(75) Inventors: Giovanni Paganelli, Pomozia (IT); Paolo Carminati, Pomezia (IT); Umberto Veronesi, Pomezia (IT)

(73) Assignee: Sigma-Tau Industrie Farmaceutiche Riunite S.p.A., Rome (IT)

( * ) Notice: Subject to any disclaimer, the term of this patent is extended or adjusted under 35 U.S.C. 154(b) by 78 days.

(21) Appl. No.: 10/554,410

(22) PCT Filed: Apr. 7, 2004

(86) PCT No.: PCT/IT2004/000184
§ 371 (c)(1),
(2), (4) Date: Nov. 17, 2005

(87) PCT Pub. No.: WO2004/093916
PCT Pub. Date: Nov. 4, 2004

(65) Prior Publication Data
US 2006/0251579 A1   Nov. 9, 2006

(30) Foreign Application Priority Data

Apr. 24, 2003 (IT) .............................. RM2003A0196

(51) Int. Cl.
*A61K 39/00* (2006.01)
*A61K 39/38* (2006.01)
*G01N 33/53* (2006.01)

(52) U.S. Cl. ...................................... 424/184.1; 435/7.1
(58) Field of Classification Search .................. None
See application file for complete search history.

(56) References Cited

U.S. PATENT DOCUMENTS

| 4,863,713 | A | 9/1989 | Goodwin et al. | |
|---|---|---|---|---|
| 6,054,122 | A * | 4/2000 | MacPhee et al. | 424/94.4 |
| 2001/0006618 | A1 * | 7/2001 | Goldenberg | 424/1.57 |
| 2003/0003051 | A1 | 1/2003 | Inverardi et al. | |
| 2003/0228256 | A1 | 12/2003 | Inverardi et al. | |
| 2004/0067199 | A1 | 4/2004 | Paganelli et al. | |
| 2005/0154275 | A1 | 7/2005 | Chinol et al. | |
| 2006/0251579 | A1 | 11/2006 | Paganelli et al. | |

FOREIGN PATENT DOCUMENTS

| EP | 0 251 494 A | 1/1988 |
|---|---|---|
| EP | 0 496 074 A | 7/1992 |
| JP | 9-506594 | 6/1997 |
| WO | 95/15979 | 6/1995 |

OTHER PUBLICATIONS

Definition of endow. American Heritage Dictionary, 2006. Houghton Mifflin Co.*
Cokgor, et al. Phase I trial results of iodine-131 labeled antitenascin monoclonal antibody 81C6 treatment of patients with newly diagnosed malignant gliomas. Journal of Clinical Oncology, 2000. vol. 18, pp. 3862-3872.*
Stendel, R., Scheurer, L., Schlatterer, K., Gminski, R., and Mohler, H. Taurolidine-fibrin-sealant-matrix using spray application for local treatment of brain tumors. Anticancer research, 2004. vol. 24, pp. 631-638.*
Rusckowski, Paganelli, Hnatowich, Magnani, Virzi, Fogarasi, Di Leo, Sudati, and Fazio. Imaging osteomyelitis with streptavidin and indium-111 labeled biotin. Journal of Nuclear Medicine, 1996. vol. 37, pp. 1655-1662.*
Samuel, Paganelli, Chiesa, Sudati, Calvitto, Melissano, Grossi, and Fazio. Detection of prosthetic vascular graft infection using avidin/indium-111 biotin scintigraphy. Journal of Nuclear Medicine, 1996. vol. 37, pp. 55-61.*
International Search Report of PCT/IT2004/000184, mailed Aug. 31, 2004.
Paganelli et al., "Pre-Targeted Locoregional Radioimmunotherapy with 90Y-Biotin in Glioma Patients: Phase I Study and Preliminary Therapeutic Results", Cancer Biotherapy and Radiopharmaceuticals, vol. 16, No. 3, 2001, pp. 227-235, XP009012633.
Paganelli et al., "Antibody-Guided Three-step Therapy for High Grade Glioma with YTTRIUM-90 Biotin", European Journal of Nuclear Medicine, vol. 26, No. 4, Apr. 1999, pp. 348-357, XP008019281.
Knox et al., "Phase II Trial of ytttium-90-DOTA-biotin pretargeted by NR-LU-10 antibody/streptavidin in patients with metastatic colon cancer", Clinical Cancer Research: An Official journal of the American Association for Cancer Research, Feb. 2000, vol. 6, No. 2, Feb. 2000, pp. 406-414, XP002292435.
Boerman et al. "Pretargeted radioimmunotherapy of cancer: Progress step by step", Journal of Nuclear Medicine, vol. 44, No. 3, Mar. 2003, pp. 400-411, XP002292436.
Chinol et al. "Biochemical modifications of avidin improve pharmacokinetics and biodistribution, and reduce immunogenicity" Bri. J. Cancer 78:189-197 (1998).
Cremonesi et al. "Three-step radioimmunotherapy with Yttrium-90 biotin: Dosimetry and pharmacokinetics in cancer patients" Eur. J. Nuclear Med. 26:110-120 (1999).
Mariani et al. "Ten year results of a randomised trial comparing two conservative treatment strategies for small size breast cancer" Eur. J. Cancer 34:1156-1162 (1998).

(Continued)

*Primary Examiner* — Anne M. Gussow
(74) *Attorney, Agent, or Firm* — Lucas & Mercanti, LLP

(57) ABSTRACT

The present invention describes the use of an agent endowed with tumour tropism in combination with another agent with anticancer activity and with an affinity for the first agent for the preparation of a medicament useful for the two-step perioperative therapy of solid tumours. The advantages of the present invention consist in the greater, effective localisation of its anticancer activity, in the reduction of the number of administration steps and in the possibility of reducing the anticancer doses, with a resulting decrease in side effects, but without any loss of efficacy.

33 Claims, No Drawings

OTHER PUBLICATIONS

Paganelli et al. "Antibody-guided three-step therapy for high grade glioma with Yttrium-90 biotin" Eur. J. Nucl. Med. 26:348-357 (1999).

Salvadori et al. "Conservative emthods for breast cancer of small size: The experience of the National cancer Institute, Milan (1973-1998)" The Breast 8:311-314 (1999).

Trikha et al. "Monoclonal antibodies as therapeutics in oncology" Curr. Opin. Biotechnol. 13:609-614 (2002).

Veronesi et al. "Twenty-year follow-up of a randomized study comparing breast-conserving surgery with radical mastectomy for early breast cancer" N. Engl. J. Med. 347:1227-1232 (2002).

Veronesi et al. "Comparing radical mastectomy with quadrantectomy, axillary dissection, and radiotherapy in patients with small cancers of the breast" N. Engl. J. Med. 305:6-11 (1981).

Veronesi et al. "Comparison of halsted mastectomy with quadrantectomy, axillary dissection, and radiotherapy in early breast cancer: Long-term results" Eur. J. Cancer Clin. Oncol. 22:1085-1089 (1986).

Veronesi et al. "Conservative treatment of early breast cancer" Ann. Surg. vol. 211:250-259 (1990).

Veronesi et al. "Breast conservation is a safe method in patients with small cancer of the breast. Long-term results of three randomised trials on 1,973 patients" Eur. J. of Cancer 31A:1574-1579 (1995).

Veronesi et al. "Radiotherapy after breast-conserving surgery in small breast carcinoma: Long-term results of a randomized trial" Ann. of Oncol. 12:997-1003 (2001).

Paganelli et al. "IART®: Intraoperative avidation for radionuclide treatment. A new way of partial breast irradiation" Breast 16:17-26 (2006).

Paganelli et al. "Intraoperative avidation for radionuclide therapy: A prospective new development to accelerate radiotherapy in breast cancer" Clin. Cancer Res. 13 (18 suppl):5646s-5651s (2007).

* cited by examiner

MEDICAMENT FOR THE TWO-STEP PERIOPERATIVE THERAPY OF SOLID TUMOURS

This application is the US national phase of international application PCT/IT2004/000184, filed 7 Apr. 2004, which designated the U.S. and claims priority of IT RM2003 A 000196, dated 24 Apr. 2003, the entire contents of each of which are hereby incorporated by reference.

The invention described herein relates to the use of reagents for the preparation of a medicament useful for intra- and postoperative locoregional and systemic therapy.

BACKGROUND TO THE INVENTION

Conservative surgery with axillary dissection and supplementary radiotherapy is the treatment of choice in patients with small-sized breast cancers. The results of recent clinical trials, particularly randomised trials (U. Veronesi, et al., *New Engl. J. Med.*, 305:6-11, 1981; U. Veronesi, et al., *Ann. Surg.* Vol. 211, 3:250-259, 1990), have shown that the risk of local recurrence of the tumour correlates with the extent of the operation on the breast, with the patient's age, and with the presence of an extensive intraductal component and peritumoral lymphatic and/or vascular invasion. In addition, a reduced incidence of local recurrence has been demonstrated in subjects undergoing supplementary radiotherapy (5.4% as against 21.6% in the control group).

The supplementary external radiotherapy currently used after surgical quadrantectomy involves the administration of a total dose of 50-60 Gy in 6 weeks of treatment, with irradiation of the entire residual breast after surgery and optionally an overdose on the operative bed. This kind of treatment regimen has by no means negligible psychological implications; its long duration increases and prolongs the patient's state of anxiety related to her experience of the disease and leads her to believe that the surgical operation has not been successful in resolving the disease. Moreover, there is also a by no means negligible social impact in terms of costs, related to the patient's absence off work for a period of about 2 months.

As an alternative to traditional radiotherapy treatment Intraoperative Radiotherapy (IORT) has recently been proposed, which is a radiotherapy technique that makes it possible to deliver a single dose of radiation directly to the tumour exposed during surgery, or to the anatomical area that contained the tumour after surgical removal of the cancer. The inventors of the present invention have used IORT with satisfactory results in the context of a randomised study for the treatment of stage T1 cancer of the breast. From the logistic point of view, however, only in a very few centres is it possible to implement this type of therapy; the cost of the equipment alone is more than one million euros, without considering the architectural costs of constructing a shielded operating theatre to guarantee radioprotection for the operators and people in the adjacent rooms and of the specialist staff necessary for implementing the treatment.

A radioimmunotherapy protocol called three-step radioimmunotherapy is known, the details of which are described in the *European Journal of Nuclear Medicament* Vol. 26, No. 2, February 1999, pp. 110-120 e No. 4, April 1999, pp. 348-357 and in European Patent EP 0 496 074. In this method, a reagent kit is used in a form suitable for intravenous administration, consisting of 1) a biotinylated monoclonal antibody specific for an antigen associated with a tumour, 2) a protein of the avidin type, 3) biotin or one of its derivatives conjugated with an efficacious agent for the treatment and/or diagnosis of a tumour. Useful agents for reducing the circulating levels of biotinylated antibody and of proteins of the avidin family (chasing agents) have also been described in the three-step radioimmunotherapy method. Such kits are indicated for intracavitary or systemic administration, but no suggestions are provided with regard to sequential administration including both the surgical act and postoperative systemic treatment.

The three-step method is undoubtedly valid in its general description, but it can be optimised and further exploited if large amounts of avidin are introduced onto the tumour or in areas of the body which could receive or which already harbour residual tumour cells after an apparently radical operation. The two main limitations of the classic three-step method consist in the fact that only modest amounts of antibodies and proteins of the avidin family, —most frequently streptavidin (steps 1 and 2)—reach the target after intravenous inoculation. The locoregional inoculation is applicable in natural anatomical cavities such as the peritoneum, pleura, or bladder, or in postoperative virtual cavities as in the case of brain tumours.

SUMMARY OF THE INVENTION

It has now been found that a perioperative-type approach, including an intraoperative locoregional step and a second postoperative systemic step, is particularly advantageous in controlling local recurrences, and, surprisingly, it has been seen that local therapy can be advantageously administered in only two steps, the first of which is performed intraoperatively in a locoregional site and the second postoperatively via a systemic route.

The introduction, during surgery, of an agent endowed with tumour tropism, that is to say, capable of concentrating locally on the tumour cell or in the vicinity of it, immediately prepares, in the residual tissue around the tumour, a sort of receptor of our choosing ready to receive, locally and in an extremely high concentration, the subsequent dose of actual anticancer agent administered intravenously. The anticancer agent must be suitably directed to the site of the tumour, exploiting the affinity of the carrier agent for the receptor artificially created.

Therefore, one initial object of the present invention is the use of a first agent endowed with tumour tropism in combination with a second anticancer agent endowed with affinity for said first agent as active ingredients for the preparation of a medicament useful for two-step perioperative therapy, the first step of which consists in an intraoperative locoregional step and the second in a postoperative systemic step. In one preferred embodiment of the invention, the therapy will take the form of radiotherapy.

Another object of the present invention is a pharmaceutical composition containing said active ingredients in separate containers (kits) suitable for sequential locoregional and systemic administration, said composition constituting a medicament useful for the adjuvant perioperative therapy of operable or not completely removable solid tumours, such as, for instance, cancers of the breast, pancreas, lung, pleura, peritoneum, face and neck, bladder, brain and others.

Advantageously, the present invention solves the problems existing in the present state of the art outlined above. An additional advantage inherent in the increased accumulation of the agent endowed with tumour tropism in the tumour site may consist in the possible reduction of the amount of anticancer agent used.

DETAILED DESCRIPTION OF THE INVENTION

In a first preferred embodiment of the invention, the therapy is immunotherapy and particularly radioimmunotherapy. Within the context of this first embodiment, the agent endowed with tumour tropism is a biotinylated antibody specific for antigens associated with a tumour.

According to the present invention, in the intraoperative step, the biotinylated antibody is administered, followed by avidin, thus constructing the "artificial receptor" for the subsequent actual anticancer agent. In this case, the anticancer agent will be carried by biotin, which will be contained in a chemical compound suitable for forming a complex with the anticancer agent and hereinafter referred to as biotin complex, and which will be administered systemically in the postoperative step.

Biotin, in fact, concentrates locally only where avidin is present and in this case one can be certain that avidin is present in the area one intends to treat, in that it was introduced by the surgeon a few hours earlier (e.g. from 4 to 72 hours) during the operation. This is a further advantage of the present invention as compared to therapy in general, in that it drastically reduces the time elapsing between removal of the primary tumour and subsequent adjuvant therapy.

The biotinylated antibody is preferably a monoclonal antibody. The antibody may be murine, human or, optionally, chimeric. Specific antibodies against antigens associated with tumours are known and available on the market or can be prepared with methods known to experts in the field, such as, for example, those described in Trikha M., et al., *Monoclonal antibodies as therapeutics in oncology, Current Opinion Biotechnology* 2002, 13:609-614. Examples of antibodies are provided in the above-mentioned European Patent EP 0 696 074. In a first preferred embodiment, the antibody is antitenascin monoclonal antibody. Chimeric or recombinant antibodies can also be used (Trikha M., et al., ibid.).

With a view to achieving maximum biotinylated antibody accumulation capacity in the target area a mixture of biotinylated monoclonal antibodies can be used, directed against different tumour antigens or against proteins of the extracellular matrix, such as tenascin. These proteins are particularly copious within the tumour and thus constitute an ideal target also after removal of the main tumour mass.

Experts in the field are familiar with antibody biotinylation.

The avidin compound used may be avidin itself which is a commercially available protein. In addition to naturally occurring avidin, other proteins of the same type can be used, e.g. streptavidin, or polymeric derivatives of avidin, streptavidin, or their derivatives with polyethylene glycol (PEGylated avidins; Chinol M., *Br. J. Cancer* 1998; 78:189-197).

The anticancer agent, which in this case will be carried by the biotin compound, may be selected from those available in the field or may be any other anticancer agent. Examples of anticancer agents are chemotherapeutic agents in general, toxins, cytokines, such as IL-2, interferon, TNF, lymphocyte cells and radionuclides, which constitute a preferred example in the present invention.

The radioactive biotin may be biotin itself labelled with a radioactive isotope by means of a special linker.

The radioisotope will be selected in relation to the specific application. Examples of suitable radioisotopes are Fe-52, Mn-52m, Co-55, Cu-64, Ga-67, Ga-68, Tc-99m, In-111, I-123, I-125, I-131, P-32, Sc-47, Cu-67, Y-90, Pd-109, Ag-111, I-131, Pm-149, Re-186, Re-188, At-211, Pb-212, Bi-212, Lu-177. As will be clear from the following description, beta-emitting radioisotopes such as Yttrium-90 or Luthetium-177 are preferred.

Though the present invention is applicable to the radioimmunotherapy of tumours in general, one preferred application is for breast, lung, pleural and peritoneal tumours.

The reagent doses will be determined by the expert in the field. They will, however, be calculated so as to deliver a dose which is sure to be tumoricidal against its target.

Indicatively, the containers of the various reagents are generally in a form suitable for injectable administration and contain an adequate quantity of reagent. In a preferred embodiment form, the container of the antibody will take the form of a special syringe equipped with one or more needles to facilitate infiltration of the tumour bed and surrounding tissue. Conveniently, the container can also be in a form suitable for administration of the antibody as a spray.

Again by way of an example, the avidin container will be suitable for containing an adequate amount of avidin, indicatively in a ratio of 5:1 to the antibody (e.g. 100 mg vs. 20 mg of antibody), optionally diluted in saline solution. In a particularly preferred form, the container will take the form of a special syringe suitable for successive administrations of precise volumes, e.g. 20 ml in the first phase and one or more further aliquots (10 ml) in a second phase of the surgery, e.g. on the resection margins or residues of diseased tissue which cannot be removed surgically because of infiltration of vital organs. Conveniently, the container may also be in a form suitable for the administration of avidin as a spray.

Preferably, the various containers, already containing the doses of the individual active ingredients, will be contained in a single pack (kit) bearing the instructions for the modes of administration.

The biotinylated antibody is administered intraoperatively, and after a certain amount of time, e.g. 10 minutes, different doses of avidin are administered, e.g. a first dose in the tumour bed, and a second dose after a possible reconstruction intervention.

Similarly, in a subsequent embodiment of the invention, avidinated antibody or avidinated antibody derivatives can be administered directly. There is a method described in the patent application by Neorx EP 0 251 494, in which a number of antibody derivatives are used systemically. The present invention differs from that method in that the step leading to the accumulation of avidin in the tumour site occurs in the operative step via the locoregional route, whereas only the administration of the biotinylated drug occurs in the postoperative step. With this procedure a kind of "artificial receptor" is created, capable of taking up radioactive biotin.

From a minimum of 4 hours to 2-3 days postoperatively, the patient will be accompanied to the nuclear medicament department to start the postoperative therapeutic step with radiolabelled biotin administered systemically. As an alternative to radiolabelled biotin, the biotin can be used as a vehicle for anticancer agents, such as, for example, chemotherapeutic agents or toxins or anticancer cells (e.g. the patient's lymphocytes). (DOTA)-$^{90}$Y/$^{177}$Lu biotin will always be administered intravenously. The initial activity will be 50 mCi, for $^{90}$Y and 80 mCi for $^{177}$Lu. On the basis of previous experience with radioimmunotherapy, these activities are ⅓ less than the maxim activity that can be administered per cycle. The therapeutic window, therefore, may range from 50 to 100 mCi for $^{90}$Y and from 80 to 150 mCi for $^{177}$Lu. Before administering the radioactive biotin, a "chaser" of biotinylated albumin can be administered, as described in the above-mentioned studies by Paganelli et al. and in EP 0 496 074, particularly, a fixed dose of 25 mg of biotinylated albumin, 10-15 minutes earlier.

Similarly, in another embodiment of the invention, avidin can be directly administered during the intraoperative locoregional phase, since it is endowed with a certain amount of tumour tropism and therefore concentrates in the therapeutic target sites.

Following these simplified procedures, many tumours that do not present specific antigens could still be treated with the reagents avidin and biotin. The sequence of the subsequent events then remains unchanged, through the time interval elapsing between the operation and the systemic therapy, which must be reduced to 4-24 hours, because the accumulation in the tumour site may require less time. The systemic administration of radiolabelled biotin or carrier agent with anticancer activity will take place as described above.

In another of its embodiments, the present invention also provides for the use of the above-mentioned active ingredients for the preparation of a diagnostic composition for pre-therapeutic biodistribution (dosimetric diagnostic phase), in which the second agent is radiolabelled. In the case of the use of beta and gamma emitters (e.g. Lu 177) such as biotinylated drugs, the dosimetric phase can be carried out at the same time as the therapeutic phase.

REFERENCES

U. Veronesi, R. Saccozzi, M. Del Vecchio, A. Banfi, C. Clemente, M. De Lena, G. Gallus, M. Greco, A. Luini, E. Marubini, G. Muscolino, F. Rilke, B. Salvadori, A. Zecchini, R. Zucali. Comparing radical mastectomy with quadrantectomy, axillary dissection, and radiotherapy in patients with small cancers of the breast. New Engl. J. Med., 305:6-11, 1981.

U. Veronesi, A. Banfi, M. Del Vecchio, R. Saccozzi, C. Clemente, M. Greco, A. Luini, E. Marubini, G. Muscolino, F. Rilke, V. Sacchini, B. Salvadori, A. Zecchini, R. Zucali: Comparison of Halsted mastectomy with quadrantectomy, axillary dissection, and radiotherapy in early breast cancer: long-term results. Eur. J. Cancer Clin. Oncol., 22: 1085-1089, 1986

U. Veronesi, B. Salvadori, A. Luini, A. Banfi, R. Zucali, M. Del Vecchio, R. Saccozzi, E. Beretta, P. Boracchi, G. Farante, V. Galimberti, G. Mezzanotte, V. Sacchini, S. Tana and E. Marubini: Conservative treatment of early breast cancer. Long-term results of 1232 cases treated with quadrantectomy, axillary dissection and radiotherapy. Ann. Surg. Vol. 211, 3:250-259, 1990.

U. Veronesi, A. Luini, M. Del Vecchio, M. Greco, V. Galimberti, M. Merson, F. Rilke, V. Sacchini, R. Saccozzi, T. Savio, R. Zucali, S. Zurrida, B. Salvadori: Radiotherapy after breast-preserving surgery in women with localized cancer of the breast. N. Eng. J. Med., vol. .328, 22:1587-1591, 1993

U. Veronesi, B. Salvadori, A. Luini, M. Greco, R. Saccozzi, M. Del Vecchio, L. Mariani, S. Zurrida and F. Rilke: Breast conservation is a safe method in patients with small cancer of the breast. Long-term results of three randomised trials on 1,973 patients. Eur. J. Cancer 31(19): 1574-1579, 1995.

L. Mariani, B. Salvadori, E. Marubini, A. R. Conti, D. Rovini, F. Cusumano, T. Rosolin, S. Andreola, R. Zucali, F. Rilke and U. Veronesi, Ten year results of a randomised trial comparing two conservative treatment strategies for small size breast cancer, European Journal of Cancer, Vol. 34, No. 8, pp. 1156-1162, 1998

Salvadori B. and U. Veronesi. Conservative methods for breast cancer of small size: the experience of the National Cancer Institute, Milan (1973-1998). The Breast 8:311-314, 1999

Veronesi U, Marubini E, Mariani L, Galimberti V, Luini A, Veronesi P, Salvadori B, Zucali R. Radiotherapy after breast-conserving surgery in small breast carcinoma: Long-term results of a randomized trial. Ann. Oncol. 12: 997-1003, 2001

Veronesi U, Cascinelli N, Mariani L, Greco M, Saccozzi R, Luini A, Aguilar M, Marubini E. Twenty-year follow up of a randomized study comparing breast-conserving surgery with radical mastectomy for early breast cancer. N. Engl. J. Med. 347: 1227-1271, 2002

The invention claimed is:

1. A method of treating a patient with a solid tumor, said method comprising:
   (a) administering intraoperatively via a locoregional route to said patient a first agent endowed with tumor tropism, wherein said first agent is selected from the group consisting of avidin, streptavidin, their polymeric derivatives and their derivatives with polyethyliene glycol capable of concentrating locally on the tumor or in the vicinity of it and then
   (b) administering postoperatively via a systemic route a second anticancer agent with affinity for said first agent, whereby increased accumulation of said first agent endowed with tumor tropism reduces the amount of said second anticancer agent to be administered.

2. The method according to claim 1 wherein said first agent is avidin.

3. The method according to claim 1, wherein said first agent is avidin and said second anticancer agent is a biotinylated anticancer agent.

4. The method according to claim 1, wherein said second anticancer agent comprises an anticancer agent selected from the group consisting of radioisotopes, chemotherapeutic agents, toxins and anticancer agents.

5. The method according to claim 4, wherein said anticancer agent is a radioisotope selected from the group consisting of Fe-52, Mn-52m, Co-55, Cu-64, Ga-67, Ga-68, Tc-99, In-111, I-123, I-125, I-131, P-32, Sc-47, Cu-67, Y-90, Pd-109, Ag-111, I-131, Pm-149, Re-186, Re-188, At-211, Pb-212, Bi-212 and Lu-177.

6. The method according to claim 5, wherein said radioisotope is Y-90 or Lu-177.

7. The method according to claim 1, wherein said solid tumor is selected from the group consisting of breast, pancreas, lung, pleural, peritoneal, cervico-facial, brain and bladder tumors.

8. The method according to claim 1, wherein said first agent and second anticancer agent are administered by injection.

9. The method according to claim 8, wherein said first agent is successively administered by syringe in precise volume.

10. The method according to claim 3, wherein said first agent is administered in a single dose.

11. The method according to claim 1, wherein said first agent is administered by spray or by injection in the tumor bed and surrounding tissue.

12. A method of treating a patient with a solid tumor, said method comprising
   (a) intraoperatively administering to the patient who is undergoing surgery, a first agent with affinity for the solid tumor, wherein said first agent is selected from the group consisting of avidin, streptavidin, their polymeric derivatives and their derivatives with polyethylene glycol, capable of concentrating locally on the tumor or in the vicinity of it, directly to said solid tumor exposed during surgery or an anatomical area containing said solid tumor after surgical removal of the cancer and then
   (b) postoperatively and systematically administering to the patient a second anticancer agent with affinity for said first agent;

thereby concentrating said second anticancer agent in the solid tumor or the anatomical area, whereby increased accumulation of said first agent in said tumor reduces the amount of said second anticancer agent to be administered.

13. The method according to claim 12, wherein said solid tumor is selected from the group consisting of breast, pancreas, lung, pleural, peritoneal, cervico-facial, brain and bladder tumors.

14. The method according to claim 12, wherein said first agent is avidin and said second anticancer agent is a biotinylated and radiolabelled antibody.

15. The method according to claim 12, wherein said first agent is avidin.

16. The method according to claim 12, wherein said second anticancer agent comprises an anticancer agent selected from the group consisting of radioisotopes, chemotherapeutic agents, toxins and anticancer agent cells.

17. A method of treating a patient with a solid tumor, said method comprising:
  (a) administering intraoperatively to the patient, who is undergoing surgery, a protein selected from the group consisting of avidin, streptavidin, a polymeric derivative of avidin, a polymeric derivative of streptavidin, a derivative of avidin with polyethylene glycol and a derivative of streptavidin with polyethylene glycol capable of concentrating locally on the tumor or in the vicinity of it, directly to said solid tumor exposed during surgery or an anatomical area containing said solid tumor after surgical removal of the cancer and then
  (b) administering postoperatively and systematically to the patient, who has undergone surgery, a biotinylated anticancer agent;
thereby concentrating said biotinylated anticancer agent in the solid tumor or the anatomical area, whereby increased accumulation of said avidin in said tumor reduces the amount of said anticancer agent to be administered.

18. The method according to claim 17, wherein said solid tumor is selected from the group consisting of breast, pancreas, lung, pleural, peritoneal, cervico-facial, brain and bladder tumors.

19. The method according to claim 17, wherein said protein is avidin.

20. The method according to claim 17, wherein said second biotinylated anticancer agent comprises an anticancer agent selected from the group consisting of radioisotopes, chemotherapeutic agents, toxins and anticancer cells.

21. The method according to claim 20, wherein said biotinylated anticancer agent is a radioisotope selected from the group consisting of Fe-52, Mn-52m, Co-55, Cu-64, Ga-67, Ga-68, Tc-99m, In-111, I-123, I-125, I-131, P-32, Sc-47, Cu-67, Y-90, Pd-109, Ag-111, 1I-131, Pm-149, Re-186, Re-188, At-211, Pb-212, Bi-212 and Lu-177.

22. The method according to claim 21, wherein said radioisotope is Y-90 or Lu-177.

23. The method according to claim 17, wherein said protein is administered by injection in the tumor bed and surrounding tissue.

24. A method of treating a patient with solid tumor, said method consisting of:
  (a) administering intraoperatively to the patient, who is undergoing surgery, a protein selected from the group consisting of avidin, streptavidin, a polymeric derivative of avidin, a polymeric derivative of streptavidin, a polymeric derivative of avidin, a polymeric derivative of streptavidin with polyethylene glycol, capable of concentrating locally on the tumor cell or in the vicinity of it, directly to said solid tumor exposed during surgery or an anatomical area containing said solid tumor after surgical removal of the cancer and then
  (b) administering postoperatively and systematically to the patient, who has undergone surgery, a biotinylated anticancer agent;
thereby concentrating said biotinylated anticancer agent in the solid tumor or the anatomical area whereby this increased accumulation of said avidin in said tumor site reduces the amount of said anticancer agent to be administered.

25. The method according to claim 24, wherein said solid tumor is selected from the group consisting of breast, pancreas, lung, pleural, peritoneal, cervico-facial, brain and bladder tumors.

26. The method according to claim 24, wherein said protein is avidin.

27. The method according to claim 24, wherein said biotinylated anticancer agent comprises an anticancer agent selected from the group consisting of radioisotopes, chemotherapeutic agents, toxins and anticancer cells.

28. The method according to claim 27, wherein said biotinylated anticancer agent is a radioisotope selected from the group consisting of Fe-52, Mn-52m, Co-55, Cu-64, Ga-67, Ga-68, Tc-99m, In-111, I-123, I-125, I-131, P-32, Sc-47, Cu-67, Y-90, Pd-109, Ag-111, I-131, Pm-149, Re-186, Re-188, At-211, Pb-212, Bi-212 and Lu-177.

29. The method according to claim 28, wherein said radioisotope is Y-90 or Lu-177.

30. The method according to claim 24, wherein said protein and said biotinylated anticancer agent are administered by injection.

31. The method according to claim 24, wherein said protein is successively administered by syringe in precise volumes.

32. The method according to claim 24, wherein said protein is administered in a single dose.

33. The method according to claim 24, wherein said protein is administered by spray or by injection in the tumor bed and surrounding tissue.

\* \* \* \* \*